(12) United States Patent
Müller et al.

(10) Patent No.: US 7,794,992 B2
(45) Date of Patent: Sep. 14, 2010

(54) ENZYMATIC SYNTHESIS, MODIFICATION AND DEGRADATION OF SILICON(IV)- AND OTHER METAL(IV)-COMPOUNDS

(75) Inventors: Werner E. G. Müller, Wiesbaden (DE); Heiko Schwertner, Schwerin (DE); Heinz C. Schröder, Wiesbaden (DE)

(73) Assignee: NanotecMARIN GmbH, Mainz (DE)

( * ) Notice: Subject to any disclaimer, the term of this patent is extended or adjusted under 35 U.S.C. 154(b) by 696 days.

(21) Appl. No.: 10/578,959

(22) PCT Filed: Nov. 9, 2004

(86) PCT No.: PCT/EP2004/012668

§ 371 (c)(1),
(2), (4) Date: Sep. 29, 2006

(87) PCT Pub. No.: WO2005/045020

PCT Pub. Date: May 19, 2005

(65) Prior Publication Data

US 2007/0280921 A1    Dec. 6, 2007

(30) Foreign Application Priority Data

Nov. 10, 2003    (DE) .............................. 103 52 433

(51) Int. Cl.
*C12N 9/00* (2006.01)
*C12N 9/02* (2006.01)

(52) U.S. Cl. ...................... 435/183; 435/189

(58) Field of Classification Search ............ None
See application file for complete search history.

(56) References Cited

FOREIGN PATENT DOCUMENTS

| DE | 100 37 270 A1 | 2/2002 |
| DE | 102 46 186 A1 | 4/2004 |
| WO | WO 00/35993 A1 | 6/2000 |
| WO | WO 02/10420 A2 | 2/2002 |

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Müller et al., "Biochemistry and Cell Biology of Silica Formation in Sponges," *Microscopy Research and Technique*, Nov. 2003, pp. 368-377, vol. 62, No. 4.
Schroeder et al., "Silicatein beta," EMBL-EBI Accession No. Q70TB1, Jul. 5, 2004.
Shimizu et al., "Tethya aurantia silicatein beta mRNA, complete cds.," EMBL-EBI Accession No. AF098670, Jan. 2, 2000.
Chinese Office Action dated May 9, 2008 in corresponding Chinese Application No. 200480040186.8.
Shimizu et al. "Silicatein α: Cathepsin L-like protein in sponge biosilica" *Proc. Natl. Acad. Sci.* USA, May 1998, pp. 6234-6238, vol. 95.
Database NCBI, Accession No. AAF21819, Shimizu et al. "Cloning of silicatein beta", Jan. 1, 2000, pp. 1-2.

* cited by examiner

*Primary Examiner*—Suzanne M Noakes
*Assistant Examiner*—Jae W Lee
(74) *Attorney, Agent, or Firm*—Saliwanchik, Lloyd & Saliwanchik

(57) ABSTRACT

The present invention relates to the use of recombinant silicatein-β or silicatein-β isolated from natural sources as well as to silicatein-β-fusion proteins as well as silicatein-β-related enzymes for the synthesis, the degradation and for modification of silicon dioxide (condensation products of silicic acid, silicates), silicones and other silicon(IV)- or metal(IV)-compounds, and their technical uses.

4 Claims, 6 Drawing Sheets

Figure 1

Figure 3:
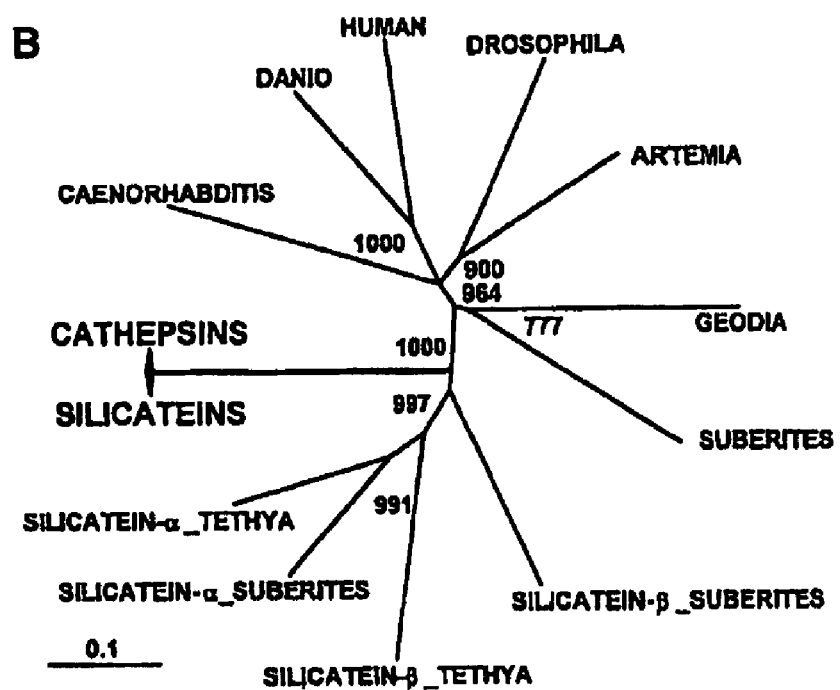

```
SEQ ID NO. 2  ACTTAGTATATTATGGTAGTGTACAATACCTATCTCCATAGAGGCATGCATAACTAGGTT   60
              TATTGAATAGCTGCTGGCACAATTTGTTCTCAAGTTGGTGCTATTAGATTTGTGTTCTAG  120
              AATGTCAGCATTGAAGTTTGTAGTTGCCTTGTGTGTAGTTCACACAAGCTTAGGAATAGC  180
SEQ ID NO. 1   M  S  A  L  K  F  V  V  A  L  C  V  V  H  T  S  L  G  I  A   20

TGAGTCAGTTGGTAAGAGCAAGACTGCAGGCCTAAGTGACGATGGCAACTACACAGCTGT  240
               E  S  V  G  K  S  K  T  A  G  L  S  D  D  G  N  Y  T  A  V   40

CACCAAATCTGTAAGACTGACTCCAGTTCTAGAGTTTGAGGAAGATTGGAAGCAATGGAC  300
               T  K  S  V  R  L  T  P  V  L  E  F  E  E  D  W  K  Q  W  T   60

AACTGATCATCACAAGGTCTACTCTGATGTGAGGGAGAGAGTGGACAAGTACACTGTATG  360
               T  D  H  H  K  V  Y  S  D  V  R  E  R  V  D  K  Y  T  V  W   80

GAGAGCTAATAAAGAGTACATTGATCAACACAACCAGAACGCACAGAGATTGGGATACAC  420
               R  A  N  K  E  Y  I  D  Q  H  N  Q  N  A  Q  R  L  G  Y  T  100

ACTCAAAATGAACAAATTTGGAGATTTGACTACCAAGGAGTTCATTGAAGGCTATCACTG  480
               L  K  M  N  K  F  G  D  L  T  T  K  E  F  I  E  G  Y  H  C  120

TGTTCAGGACTACCAACCTACCAATGCATCACATTTGAATAAGAAACACAAAACGCACGC  540
               V  Q  D  Y  Q  P  T  N  A  S  H  L  N  K  K  H  K  T  H  A  140

GTTTGTCGACTATGGTGACTTTGTGAGGGGTGGAACTGGTGAGGGTGTGAGGGGTGTAGG  600
               F  V  D  Y  G  D  F  V  R  G  G  T  G  E  G  V  R  G  V  G  160

AAACATGCCGGAGACTATGGACTGGAGAACTTCTGGAGTTGTCACAAAAGTTAAAGATCA  660
               N  M  P  E  T  M  D  W  R  T  S  G  V  V  T  K  V  K  D  Q  180

GCTTCGTTGTGGTAGCAGCTATGCGTTCTCTGCCATGGCTTCATTGGAAGGAATAAATGC  720
               L  R  C  G  S  S  Y  A  F  S  A  M  A  S  L  E  G  I  N  A  200

TCTTTCCTACGGATCTTTGGTGACACTCAGTGAACAAAACATTGTAGACTGCTCGGTTAC  780
               L  S  Y  G  S  L  V  T  L  S  E  Q  N  I  V  D  C  S  V  T  220

CTATGGCAACCATGGTTGCGCCTGTGGTGATGTAAACCGTGCTCTACTGTATGTGATAGA  840
               Y  G  N  H  G  C  A  C  G  D  V  N  R  A  L  L  Y  V  I  E  240

GAATGATGGCGTTGACACGTGGAAGGGTTATCCTTCTGGTGGGGATCCTTATCGATCAAA  900
               N  D  G  V  D  T  W  K  G  Y  P  S  G  G  D  P  Y  R  S  K  260

GCAATACTCTTGCAAATACGAGAGACAGTATCGTGGGGCCTCTGCTAGAGGTATAGTCAG  960
               Q  Y  S  C  K  Y  E  R  Q  Y  R  G  A  S  A  R  G  I  V  S  280

TCTAGCTAGTGGTGATGAGAACACATTGTTGACAGCAGTAGCTAACTCTGGACCAGTGAG 1020
               L  A  S  G  D  E  N  T  L  L  T  A  V  A  N  S  G  P  V  S  300

TGTGTATGTGGACGCTACTTCAACATCCTTCCAGTTTTACAGTGATGGAGTGTTGAATGT 1080
               V  Y  V  D  A  T  S  T  S  F  Q  F  Y  S  D  G  V  L  N  V  320

TCCCTATTGCTCCTCTAGCACGCTGAGTCATGCCTTGGTTGTCATTGGTTACGGGAAGTA 1140
               P  Y  C  S  S  S  T  L  S  H  A  L  V  V  I  G  Y  G  K  Y  340

CAGCGGACAAGATTACTGGCTTGTTAAAAACAGCTGGGGTCCTAACTGGGGAGTGCGGGG 1200
               S  G  Q  D  Y  W  L  V  K  N  S  W  G  P  N  W  G  V  R  G  360

CTATGGGAAGTTGGCAAGAAACAAGGGCAACAAATGTGGAATAGCCACAGCGGCTAGTTT 1260
               Y  G  K  L  A  R  N  K  G  N  K  C  G  I  A  T  A  A  S  F  380
```

Figure 1 cont.

```
CCCAACATTATGACACTTTAGTTGATCAAACAATTAATCATAAATTATTACAACATGTAG  1320
  P   T   L                                                    383

TATAATGATGCCCCCCCATTGCTCAATAGCTTATCTTTGAACAAGAAAAAAA          1370
```

Figure 2

ENZYMATIC SYNTHESIS, MODIFICATION AND DEGRADATION OF SILICON(IV)- AND OTHER METAL(IV)-COMPOUNDS

This application is a National Stage Application of International Application Number PCT/EP2004/012668, filed Nov. 9, 2004; which claims priority to German Application No. 103 52 433.9, filed Nov. 10, 2003.

The present invention relates to the use of recombinant silicatein-β or silicatein-β isolated from natural sources as well as to silicatein-β-fusion proteins as well as silicatein-β-related enzymes for the synthesis, the degradation and for modification of silicon dioxide (condensation products of silicic acid, silicates), silicones and other silicon(IV)- or metal(IV)-compounds, and their technical use.

1. STATE OF THE ART

Silicon-compounds, such as silicates and silicones (siloxanes) are widely used materials in industry and medicine, and are also important from an economic point of view. Many high-technology-products, such as optical and microelectronic instruments, as well as catalysts contain or consist of silicates or silicone-compounds.

The tetraedrically designed silicate-anion ($[SiO_4]^{4-}$; monomer) tends to a polymerization by linking of $SiO_4$-units, whereby two Si-atoms each are connected with each other by an O-atom. Thereby, first ortho-disilicic acid (pyrosilicic acid; $H_6Si_2O_7$) is generated from the ortho-silicic acid by cleaving off water (condensation). The further condensation via the poly-silicic acids leads to the meta-silicic acids $[(H_2SiO_3)_n]$. At smaller numbers of the $SiO_4$-units (n=3, 4 or 6), also ring-shaped molecules can be formed. Upon further progression of the condensation, three-dimensional structures corresponding to the composition $SiO_2$ are generated from the chains or nets that are obtained first (CD Römpp Chemistry lexicon—Version 1.0, Stuttgart/New York: Georg Thieme Verlag 1995).

The (polymeric) silicon dioxide ($SiO_2$) can be found both in crystalline as well as in amorphous form. Quartz, tridymite, and cristobalite, amongst others, are belonging to the different forms of crystalline $SiO_2$. Amorphous silicon dioxide-minerals are, amongst others, agate, opal, and flint stone. Many skeletal structures which are generated by bio-mineralization consist of amorphous $SiO_2$ (also named silica), such as the shells of siliceous algae (diatoms), and the needles (spiculae) of siliceous sponges. In all of these $SiO_2$-forms, silicon has the coordination number 4, and is tetraedrically surrounded by four oxygen-atoms.

By a partial replacement of the OH-groups of the silicic acid by single-bond organic residues that are not involved in the condensation process, different silicones (siloxanes) are generated. They are grouped into linear, branched and cyclic polysiloxanes, as well as cross-linked polymers (linking of chain- or ring-shaped molecules into two- or three-dimensional networks).

The viscosity of the silicones (silicone oils) that are of a chain-form increases with increasing length of the chain. Silicones that are cross-linked to a lower extent, exhibit natural rubber-elasticity (silicone natural rubber), highly cross-linked chains are resin-like (silicone-resins).

The present invention relates to the use of recombinant silicatein-β, or silicatein-β isolated from natural sources as well as to silicatein-β-fusion proteins for a synthesis and the degradation of amorphous or crystalline silicon dioxide (silicic acids and silicates), siloxanes as well as modifications of these compounds, and their technical uses.

The present invention also relates to the use of recombinant silicatein-β, or silicatein-β isolated from natural sources as well as to silicatein-β-fusion proteins for the identification of activators or inhibitors of these processes that are catalyzed by the enzyme.

1.1 Bio-mineralization (Formation of Biogenic Silicon Dioxide) in Siliceous Sponges)

The technical synthesis of the silicates requires drastic conditions, such as high pressure and high temperature. In contrast, siliceous sponges—like the siliceous algae—are able to form silicate scaffolds with the aid of specific enzymes at mild conditions, i.e. at relatively low temperature and low pressure.

The main elements of the skeleton of the siliceous sponges are the needle-shaped spiculae that, in the group of the demo-sponges (horn sponges) and hexactinellida (glass sponges), consist of amorphous non-crystalline silicon dioxide.

The state of the knowledge regarding the morphology and biogenesis of the spiculae is reviewed in: Uriz et al. (2003) Progr Molec Subcell Biol 33:163-193; Müller et al. (2003) Progr Molec Subcell Biol 33:195-221. The opal silicon dioxide in the sponge-spiculae contains 6-13% water, resulting in the approximate formula $(SiO_2)_{2-5} \cdot H_2O$ (Schwab & Shore (1971) Nature 232:501-502). In demosponges, the spiculae formation starts around an axial filament about which the silica is deposited enzymatically.

Two enzymes that are involved in the synthesis and/or the degradation of the $SiO_2$-skeleton in silicate-forming organisms and their technical uses were described.

One enzyme is silicatein-α (also simply designated silicatein), the other one is the protein which produces the axial filament that fills the axial channel of the sponge-spiculae (needles) (PCT/US99/30601. Methods, compositions, and biomimetic catalysts, such as silicateins and block co-polypeptides, used to catalyze and spatially direct the polycondensation of silicon alkoxides, metal alkoxides, and their organic conjugates to make silica, polysiloxanes; polymetallo-oxanes, and mixed poly(silicon/metallo)oxane materials under environmentally benign conditions. Inventors/Applicants: Morse D E, Stucky G D, Deming, T D, Cha J, Shimizu K, Zhou Y; DE 10037270 A1. Silicatein-mediated synthesis of amorphous silicates and siloxanes and their use. German Patent Office 2000. Applicants and Inventors: Müller W E G, Lorenz B, Krasko A, Schröder H C; PCT/EP01/08423. Silicatein-mediated synthesis of amorphous silicates and siloxanes and use thereof. Inventors/Applicants: Müller W E G, Lorenz B, Krasko A, Schröder H C). This enzyme was cloned from the marine siliceous sponge *Suberites domuncula* (Krasko A, Batel R, Schröder H C, Müller I M, Müller W E G (2000) expression of silicatein and collagen genes in the marine sponge *S. domuncula* is controlled by silicate and myotrophin. Europ J Biochem 267:4878-4887). Silicatein is able to synthesize amorphous silicon dioxide (polysilicic acids and polysilicates) from organic silicon compounds (alkoxysilanes) (Cha J N, Shimizu K, Zhou Y, Christianssen S C, Chmelka B F, Stucky G D, Morse D E (1999) Silicatein filaments and subunits from a marine sponge direct the polymerization of silica and silicones in vitro. Proc Natl Acad Sci USA 96:361-365).

The second enzyme is silicase, which belongs to the group of the carboanhydrases (DE 102 46 186.4. Degradation and modification of silicates and silicones through silicase and use of the reversible enzyme. German Patent Office 2002. Applicants and Inventors: Müller W E G, Krasko A, Schröder H C). This enzyme, which was first discovered in the marine sponge *S. domuncula*, is primarily involved in the degradation of biogenic silica (Schröder H C, Krasko A, Le Pennec G, Adell T, Wiens M, Hassanein H, Müller I M, Müller W E G (2003) Silicase, an enzyme which degrades biogenous amorphous silica: Contribution to the metabolism of silica deposition in the demosponge *Suberites domuncula*. Progr Molec Subcell Biol, 33, 250-268) but can also synthesize it in the reversible reaction.

2. MATTER OF THE INVENTION

It was surprisingly discovered by inventors—first in the marine sponge *S. domuncula*—that in cells of silica-forming organisms not only one silica-synthesizing enzyme (silicatein-α), but additional silica-forming enzymes can be found. Thereby, the silicatein-β as described here is characterized by particularly advantageous properties in view of its catalytic abilities and their technical/medicinal use that can not be derived from the state of the art, and analogous conclusions, by the person of skill.

These advantageous properties are based on:
a) Different substrate specificity
b) Different kinetics
c) Different binding constants
d) Different stability.

The cDNA that encodes for the silicatein-β-polypeptide was isolated from *S. domuncula* using the PCR-method (see below). Related cDNAs can also be isolated from other sponges, such as, for example, *Geodia cydonium*.

The present invention is furthermore novel in that the silicatein-β-gene can be induced in animals (sponges) or cells/cellular aggregates obtained therefrom by increasing the silicon-concentrations in the medium (usually to 60 µM silicate or another silicon compound, the hydrolysis of which results in a like concentration of silicate). Particularly advantageous is (an even stronger induction is achieved), if in addition to silicon also in increased concentration of ion (ferric ions or ferric salts or complexes, such as Fe(+++)citrate) is present in the medium.

According to a further aspect of the present invention, generally a method for the in vitro or in vivo synthesis of silicon dioxide (condensation products of silicic acid or silicates), silicones and other silicon(IV)- or metal(IV)-compounds as well as of mix-polymers of these compounds is provided, wherein a polypeptide or a metal complex of a polypeptide is used for the degradation, characterized in that the polypeptide comprises an animal, bacterial, plant or fungal hydrolase (silicatein-β)-domain that has at least 25% sequence similarity (see FIG. 1) to the sequence as depicted in SEQ ID No.1. It was yet unknown and not to be recognized from the state of the art that in addition to silicatein-α further enzymes like the silicatein-β as described herein are able to produce silicates or silicones. Due to the reversibility of these processes, a further aspect of the present invention relates to a method the degradation of amorphous silicon dioxide (condensation products of silicic acid or silicates), silicones and other silicon(IV)- or metal(IV)-compounds as well as of mix-polymers of these compounds, wherein a polypeptide or a metal complex of a polypeptide is used for the synthesis, characterized in that the polypeptide comprises an animal, bacterial, plant or fungal hydrolase (silicatein or cathepsin)-domain that has at least 25% sequence similarity to the sequence as depicted in SEQ ID No. 1.

A method according to the invention is used that is characterized in that for the synthesis compounds such as silicic acids, monoalkoxysilanetrioles, monoalkoxysilanedioles, monoalkoxysilanoles, dialkoxysilandioles, dialkoxysilanoles, trialkoxysilanoles, tetraalkoxysilanes, alkyl-, aryl- or metallo-silanetrioles, alkyl-, aryl- or metallo-silandioles, alkyl-, aryl- or metallo-silanoles alkyl-, aryl- or metallo-monoalkoxysilanedioles, alkyl-, aryl- or metallo-monoalkoxysilanoles, alkyl-, aryl- or metallo-dialkoxysilanoles, alkyl-, aryl- or metallo-trialkoxysilanes or other metal (IV)-compounds are used as reactants (substrates). By using defined mixtures of the compounds, wherein the ratio of the substrates can be freely chosen, mix-polymers of a defined composition can be produced.

According to a further aspect of the present invention, the formation of defined two- and three-dimensional structures can take place by the polypeptide or a metal complex of the polypeptide or the binding of the polypeptide or a metal complex of the polypeptide to other molecules or the surfaces of glass, metals, metal oxides, plastics, biopolymers or other materials as template.

According to a further aspect of the present invention a method for modifying a structure or surface containing a silicic acid or silicon(IV)- or metal(IV)-compound is provided, wherein a polypeptide or a metal complex of a polypeptide is used for the modification, characterized in that the polypeptide comprises an animal, bacterial, plant or fungal hydrolase (silicatein or cathepsin)-domain that has at least 25% sequence similarity to the sequence as depicted in SEQ ID No. 1. Preferably, the structure or surface containing silicic acid is present in form of a precious stone or a semi-precious stone.

A method according to the invention is employed, wherein the modification is comparable to a smoothening, a slight etching or comprises the production of borings or recesses of the structure or surface containing a silicic acid or silicon (IV)- or metal(IV)-compound by the polypeptide or a metal complex of the polypeptide.

A further aspect of the present invention relates to a chemical compound or structure or surface containing silicic acid which was obtained with a method according to the invention, in particular in form of a precious stone or a semi-precious stone.

A further aspect of the present invention also relates to a polypeptide of a hydrolase (silicatein-β) from *Suberites domuncula* according to SEQ ID No. 1 or a polypeptide that is homologous thereto, which exhibits at least 25% sequence similarity to the sequence as depicted in SEQ ID No. 1 in the amino acid sequence of the hydrolase (silicatein-β)-domain, a metal complex of the polypeptide, or parts thereof.

A further aspect of the present invention also relates to a nucleic acid, in particular according to SEQ ID No. 2, characterized in that it essentially encodes for a polypeptide according to the invention. The nucleic acid according to the invention can be present in the form of a DNA, cDNA, RNA or mixture thereof and can be characterized in that the sequence of the nucleic acid has at least one intron and/or a polyA-sequence. Another aspect of the present invention relates to the nucleic acid according to the invention in form of its complementary "antisense"-sequence.

An even further aspect of the present invention also relates to a nucleic acid according to the invention in form of a (a) fusion protein-(chimeric protein) construct, (b) a construct having separate protein-expression (protease-cleavage site) or (c) a construct with separate protein-expression (cassette-expression). The nucleic acid according to the invention can be produced synthetically. Methods for this are well known in the state of the art.

A further aspect of the present invention relates to a vector, preferably in form of a plasmid, shuttle vector, phagemid, cosmid, expression vector, retroviral vector, adenoviral vector or particle, nanoparticles or liposomes, wherein the vector contains a nucleic acid according to the invention. Furthermore, vectors for a transfer of proteins can be provided, preferably in form of a nanoparticle or liposome that comprises a polypeptide of the invention.

According to a further aspect of the present invention, a host cell is provided that is transfected with a vector or infected or transduced with a particle according to the invention. This host cell can be characterized in that it expresses a polypeptide according to claim 1, a metal complex of the polypeptide or parts thereof. Suitable as host cell are all known host cell-organisms, such as yeasts, fungi, sponges, bacteria, CHO-cells or insect cells.

The polypeptide according to the invention can, in addition to the natural form, be further characterized in that it was synthetically produced or that the polypeptide or the metal complex of the polypeptide is present in a prokaryotic or eukaryotic cellular extract or lysate. The cellular extract or the lysate can be obtained from a cell ex vivo or ex vitro, for example a recombinant bacterial cell or a marine sponge.

The polypeptide according to the invention can be purified according to common methods that are known in the state of the art, and therefore can be present essentially free from other proteins.

A further aspect of the present invention then relates to a method for identifying of inhibitors or activators of a polypeptide of a hydrolase (silicatein-β) from *Suberites domuncula* according to SEQ ID No. 1 or a polypeptide that is homologous thereto, which in the amino acid sequence of the hydrolase (silicatein-β)-domain exhibits at least 25% sequence similarity to the sequence as depicted in SEQ ID No. 1, wherein a) a polypeptide of a hydrolase (silicatein-β) from *Suberites domuncula* according to SEQ ID Nr. 1 or a polypeptide that is homologous thereto, which in the amino acid sequence of the hydrolase (silicatein-β)— domain exhibits at least 25% sequence similarity to the sequence as depicted in SEQ ID No. 1, is provided, b) the polypeptide from step a) is contacted with a potential inhibitor or activator, and c) the ability of the polypeptide is measured, to synthesize or degrade silicates or silicones. With these methods, valuable substances can be detected which under certain circumstances are suitable as therapeutics (for this, see in the following). Methods for identifying such substances are known to the person of skill and e.g. include the use of radioactively labeled or enzymatically labeled candidate-compounds. Methods for measuring the activity of the hydrolase (silicatein-β) are described in the following and can be readily adapted by the person of skill to a particular assay format. Thereby, an inhibitor essentially completely reduces the activity of the enzyme, an activator induces an activity or enhances this above the base level.

According to an alternative of the method, the polypeptide of a hydrolase (silicatein-β) from *Suberites domuncula* according to SEQ ID No. 1 or a polypeptide that is homologous thereto that in its amino acid sequence of the hydrolase (silicatein-β)-domain exhibits at least 25% sequence similarity to the sequence as depicted in SEQ ID No. 1 can be provided for the assay in vivo, in a prokaryotic or eukaryotic cellular extract or lysate or in a purified form.

An even further aspect of the present invention relates to a method for producing a pharmaceutical composition, comprising a) identifying of an inhibitor or activator and b) mixing of the identified inhibitor or activator with a pharmaceutically acceptable carrier or auxiliary agent. By means of this composition valuable pharmaceutics are provided that, like the polypeptide or a nucleic acid of the invention, can be used for the prevention or therapy of silicosis. Furthermore, the use of a polypeptide or a nucleic acid or pharmaceutical composition according to the invention for the resorption or for a modulation of the resorbability of silicones and silicone-implants can occur. Finally, the present invention can also be used for a transfection of cells with nucleic acids according to the invention for a resorption or for a modulation of the resorbability of silicones and silicone-implants. The above indicated uses and the methods related thereto are known to the person of skill and can readily be adjusted for the needs and requirements as present here.

The invention shall now be further illustrated in the following examples, without being limited thereto. In the attached Figures and the sequence protocol, it is shown that:

In the following, the explanatory legends for the attached Figures and the sequence protocols are listed. They show:

SEQ ID No. 1: The amino acid sequence of the silica-metabolic silicatein-β-polypeptide according to the invention from *S. domuncula* (rSILICAβ_SUBDO), SEQ ID No. 2: The nucleic acid sequence of the cDNA of the silica-metabolic silicatein-β-polypeptide according to the invention from *S. domuncula*.

FIG. 1:

The nucleic acid sequence (SEQ ID No. 2) of the cDNA of the silica-metabolic silicatein-β-polypeptide according to the invention from *S. domuncula*. The amino acid sequence (SEQ ID No. 1) as derived from the nucleotide sequence of the open reading frame is indicated below the nucleotide sequence.

FIG. 2:

Shown is a comparison ("alignment") of the sponge-silicatein-sequences, silicatein-α and silicatein-β, from *S. domuncula* (SILICAaSUBDO [GenBank Database-Accession-Number CAC03737.1](SEQ ID No. 3), and SILICAb-SUBDO [AJ519940])(SEQ ID No. 1), and *T. aurantium* (SL-LICAaTETHYA [AAC23951.1](SEQ ID No. 4); SILICAbTETHYA [AF098670]) (SEQ ID No. 5). Conserved residues (similar or related in view of their physical-chemical properties) in the sequences are shown in white on black, and those in at least two sequences in black on grey. The characteristic positions within the silicatein-sequences are indicated: Ser (●), His (■), and Asn (■), the processing site for the conversion of the pro-enzyme into the mature enzyme is indicated (}{), as well as the serine-cluster ([Ser]).

FIG. 3:

Phylogenetic relations of the sponge-silicatein with the cathepsin L-sequences of protostomia (*D. melanogaster* [DROSOPHILA] BAA06738; *Caenorhabditis elegans* [CAENORHABDITIS] NP_507199; *Artemia franciscana* [ARTEMIA] AAD39513) and deuterostomia (*Danio rerio* [DANIO] AAN32912.1; *Homo sapiens* [HUMAN] X12451), together with the sponge sequences from *S. domuncula* ([SUBERITES]; AJ272013) and *G. cydonium* ([GEODIA]; Y10527). The tree remained "un-rooted" [without outside group "root"], in order to the show the clustering of the cathepsins and silicateins. The numbers at the branching indicate the statistic significance of the branchings (1000 corresponds to 100% significance). The scale indicates the so-called "evolutionary distance", wherein the length of the scale corresponds to a distance z of 0.1 amino acid-substitutions per position within the sequence.

FIG. 4:

Amount of the expression of silicatein in tissue of *S. domuncula* after transfer into silicate/Fe(+++)-supplemented artificial sea-water. The RNA was either extracted immediately after the addition of silicate/Fe(+++) (day zero), or two and six days later. Northern-blot-analysis.

FIG. 5:

Detection of silicatein-positive cells in sponge tissue. (A) Cryosections were produced from a sponge that was held in silicate/Fe(+++)-free sea-water, and hybridized with DIG-labeled SDSILICAβ-antisense DNA. Subsequently, the samples were incubated with anti-digoxigenin/alkaline phosphatase, and the signals were detected with NBT/X-phosphate. Analysis of the sections of animals that were held for 2 (B), 4 (C) or 6 days (D) in silicate/Fe(+++)-supplemented sea-water. The channels (c) of the water-containing system within the mesohyl (m) are shown. The channels were delimited by an epithelial layer that is formed by pinacocytes. Magnification: ×50.

Cloning of the Gene Encoding for Silicatein-β

A cDNA encoding for the silicatein-β of S. domuncula was isolated from a cDNA-library (FIG. 1). In the case of silicatein-β, until now, it was merely known that the enzyme can be found as a protein component of the axial filaments of the spiculae (sponge-needles), but not its participation in the enzymatic formation of silicon dioxide spiculae.

The isolation of the cDNA for silicatein-β, e.g., from S. domuncula is performed as follows. For the homology-screening, a digoxigenin-11-dUTP-labeled DNA-probe ("DIG random primed DNA labeling kit"; Co. Roche) of Silicatein-α from S. domuncula is used; the sequence of this cDNA is described (Database-Accession-Number AJ272013; Krasko et al. (2000) Europ J Biochem 267:4878-4887). The screening of the S. domuncula-cDNA-library is performed under "low stringency"—hybridization conditions for the "plaque lifts", as described (Kruse et al. (1997) Mol Biol Evol 14:1326-1334). Positive clones were identified with an alkaline phosphatase-conjugated anti-digoxigenin-antibody, using BCIP/NBT as a substrate (Blake et al. (1984) Anal Biochem 136:75-179). It can be determined by Northern-blotting, whether the complete sequence SDSILICAβ was obtained. The DNA-sequencing can be performed with an automatic DNA-sequencer (Li-Cor 4000S).

The cDNA encoding for the silicatein-β-polypeptide from the marine sponge S. domuncula as well as the polypeptide derived from said nucleotide sequence have the following characteristics. The nucleotide sequence comprises 1372 residues, with an open reading frame from $nt_{122-124}$ to $nt_{1271-1273}$ (stop codon) (FIG. 1). The amino acid sequence of the silicatein-β as derived, with 383 residues, represents a polypeptide with a size of 42,068 (FIG. 1 and FIG. 2).

The sponge-silicatein-β-polypeptide is a novel member of the cathepsin L subfamily (Shimizu et al. (1998) Proc Natl Acad Sci USA 95:6234-6238; Cha et al. (1999) Proc Natl Acad Sci USA 96:361-365; Krasko et al. (2000) Europ J Biochem 267:4878-4887). The S. domuncula-Silicatein-β-polypeptide shares the largest similarity with silicatein-α from Tethya aurantium (Database-Accession-Number AAC23951.1; "Expect value" [E; Blast-NCBI; (Coligan et al. (2000) Current Protocols in Protein Science. John Wiley & Sons, Chichester)]=$7e^{-58}$), with silicatein-β from T. aurantium (AF098670; E=$4e^{-57}$), and with silicatein-β from S. domuncula (CAC03737.1; E=$2e^{-56}$); the S. domuncula silicatein-β is slightly further related to cathepsin L from Rhodnius prolixus (AF320565; E=$3e^{-55}$). All four silicatein sequences show the characteristic three amino acids Ser (instead of Cys that is present in the cathepsins), His and Asn, which form the catalytic triad of the cysteine-proteases (Shimizu et al. (1998) Proc Natl Acad Sci USA 95:6234-6238; Cha et al. (1999) Proc Natl Acad Sci USA 96:361-365; Krasko et al. (2000) Europ J Biochem 267:4878-4887); FIG. 2. The processing site that is required for the formation of the active enzyme, either as result of an autolysis or by a second protease, can be predicted according to: Nishimura et al. ((1988) Arch Biochem Biophys 261:64-71). Based on comparisons with the cathepsins, the cleavage site in the sponge-silicatein-β can be localized at $aa_{139}$ (FIG. 2); thus, the pro-enzyme with $M_r$ 42,068 Da will mature into an active enzyme with a predicted $M_r$ of 26,205 Da. The three hypothetical disulfide-bridges are present in the sponge-silicatein-β, like in the other cysteine-proteases.

Phylogenetic Analysis of the Silicatein-β-polypeptide

For the phylogenetic analysis (FIG. 3), a comparison ("alignment") of the sponge-silicateins from S. domuncula (silicatein-α and silicatein-β) and T. aurantium (silicatein-α and silicatein-β) with the cathepsin L-sequences from protostomia (Drosophila melanogaster, Caenorhabditis elegans and Artemia franciscana) and deuterostomia (Homo sapiens and Danio rerio) together with the cathepsin-sequences from S. domuncula and G. cydonium was performed. The "unrooted" tree [without outside group "root"] shows that the cathepsin L-sequences are clearly separated from the four silicateins.

Up-Regulation of the Silicatein-β-polypeptide

The expression of the silicatein-β-gene can be up-regulated by the addition of silicate and Fe(+++) into the medium. This can be exemplary shown by Northern-blotting or Western-blotting on whole animals, tissues, cells or cellular aggregates (such as sponge-primmorphs).

The latter primmorphs are aggregates that consist of proliferating and differentiating cells, and are formed from individual sponge cells. A patent was filed for the primmorph-system (DE 19824384. Production of primmorphs from dissociated cells from sponges, corals and further invertebrates: Culturing-method of cells from sponges and further invertebrates for the production and detection von bioactive substances, for a detection of environmental toxins, and for culturing of these animals in aquaria and outdoor. Inventors and Applicants: Müller W E G, Brümmer F).

Figure 4:
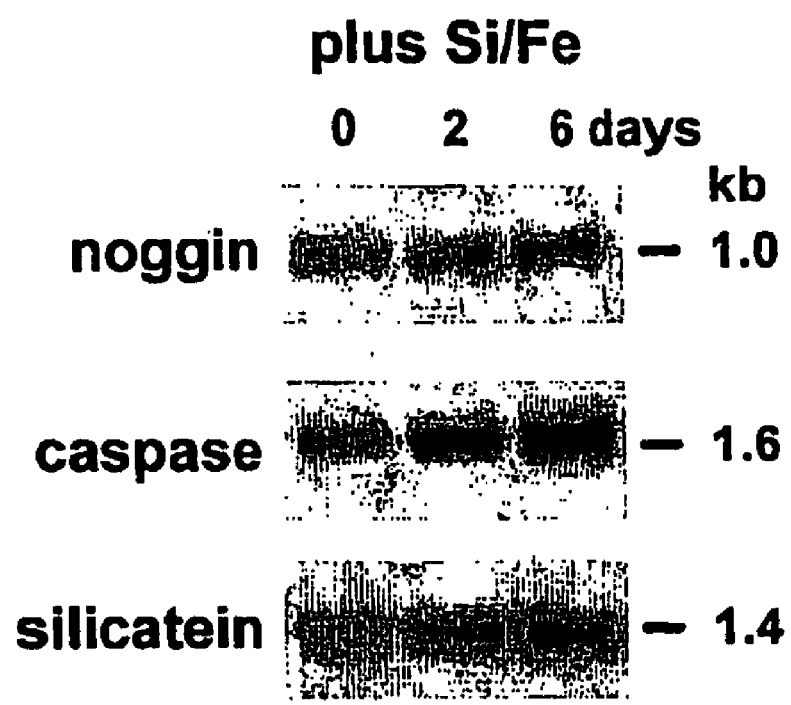

In the experiment as shown in FIG. 4, the amount of the expression of the silicatein-β-gene was determined, which is strongly up-regulated in response to silicate and Fe(+++) in the medium.

For determining the effect of silicon and ion on the gene expression, the animals were cultured for two weeks in artificial sea-water which is composed of chloride (19.0 g/kg), sodium (11.0), magnesium (1.3), sulfate (2.7), calcium (0.4), potassium (0.4), and bicarbonate (0.15). Then, the animals were transferred into artificial sea-water, supplemented with 60 μM silicate (in the form of Na-silicate), and 30 μM Fe(+++).

Northern-blotting

The RNA is extracted from animals, tissues, cells or cellular aggregates pulverized in liquid nitrogen with TRIzol-reagent (Fa. GibcoBRL). Then, an amount of 5 μg total-RNA is electrophoretically separated on a 1% formaldehyde/agarose-gel, and blotted on a HYBOND-N⁺-nylon-membrane in accordance with the instructions of the manufacturer (Co. Amersham). The hybridization is performed with the cDNA SDSILICAβ. A silicatein-μ-probe can be used, for example, that reaches from $nt_{676}$ to $nt_{1198}$, and thus spans the characteristic region in the derived polypeptide, namely the serine-rich cluster. This cluster is found in the S. domuncula silicatein-β-polypeptide between $aa_{309}$ to $aa_{329}$; this region also exhibit differences with the silicatein-α-polypeptide. As internal standard, for example, the S. domuncula β-tubulin cDNA, SDTUB (GenBank Database-Accession-Number AJ550806) can be used. The probes are labeled with the PCR-DIG-probe-synthesis kit in agreement with the "instruction manual" (Co. Roche). After washing, the DIG-labeled nucleic acid is detected with the anti-DIG Fab-fragments, [conjugated to alkaline phosphatase; dilution 1:10,000], and visualized through chemoluminescence technique using CDP in agreement with the instructions of the manufacturer (Co. Roche). Then, the screenings can be scanned for analysis, e.g, with a GS-525 MOLECULAR IMAGER (Co. Bio-Rad).

The examinations of the Northern-blots showed that the amounts of transcripts strongly increase after transfer of the animals from silicate/Fe(+++)-free into silicate/Fe(II)-containing sea-water (FIG. 4). Parallel hybridization studies with the SDTUB (β-tubulin) gene showed that the identical amount of RNA was loaded onto the gels.

Based on these results, it can be concluded that in intact animals silicatein-β-positive cells are formed after incubation of the animals with silicate/Fe(+++).

In situ-localization Studies

The expression of the silicatein-β-gene can also be followed by means of in situ-hybridization. For this, tissue of animals, e.g. after 6-day incubation in a silicate/Fe(+++)-medium, is treated in sea-water, supplemented with 30 mM ethylenediaminetetraacetic acid (EDTA) for 30 min at room temperature. The spiculae are then obtained by sedimentation, and further processed for the in situ-hybridization.

In the following, a method is used which is based on the procedure as described by Polak & McGee (In situ hybridization. Oxford University Press, Oxford, 1998), with modifications (Le Pennec et al. (2003) J Biotechnol 100:93-108). 8-μm thick frozen sections were obtained at −30° C. with the aid of a cryostat. The cyrosections are fixed with paraformaldehyde, and then washed 2 times with 1×PBS at room temperature. The sections are incubated with proteinase K, and subsequently fixed again with paraformaldehyde. In order to remove the sponge color, the sections are incubated with ethanol, and finally with isopropanol. Following the rehydration with 1×PBS, the digoxigenin(DIG)-labeled DNA-probes are added to the hybridization solution. The hybridization is performed over night in a glass container at 45° C.; the subsequent washing steps are performed at 50° C. as described (Perović et al. (2003) Evo & Devo 5:240-250). After blocking the sections are incubated, e.g., with an anti-digoxigenin-antibody that is conjugated with alkaline phosphatase. For the visualization of the signals the color reagent NBT/X-phosphate can be used.

Production of DNA-probes for in situ-localization Studies

The in-situ-hybridization, for example, can be performed with a digoxigenin-labeled ssDNA-probe. The probe is labeled, e.g., with the "PCR DIG probe synthesis kit" (Co. Roche). The DNA-probe is designed based on the S. domuncula cDNA-sequence. Both antisense as well as sense probes are produced by polymerase chain reaction (PCR) using the linearized cDNA. The antisense probe is obtained by using a "forward primer" in 5' to 3' sense direction; the complementary sense probe is obtained by using a reverse primer in the 3' to 5' orientation. The SDSILICAβ-probe spans a segment within the open reading frame with a length of 520 bp ($nt_{676}$ to $nt_{1198}$). The PCR, for example, is performed with the aid of a GeneAmp 9600 thermal cycler (Perkin Elmer). The following reaction conditions have proven to be suitable in the PCR: initial denaturation at 95° C. for 3 min, 35 amplification cycles each at 95° C. for 30 sec, 58° C.-30 sec, 74° C.-4 min, and a final extension step at 72° C. for 20 min. The labeling, for example, can be done using the "DIG oligonucleotide labeling kit" (Co. Roche).

Silicatein-positive Cells

Figure 5:
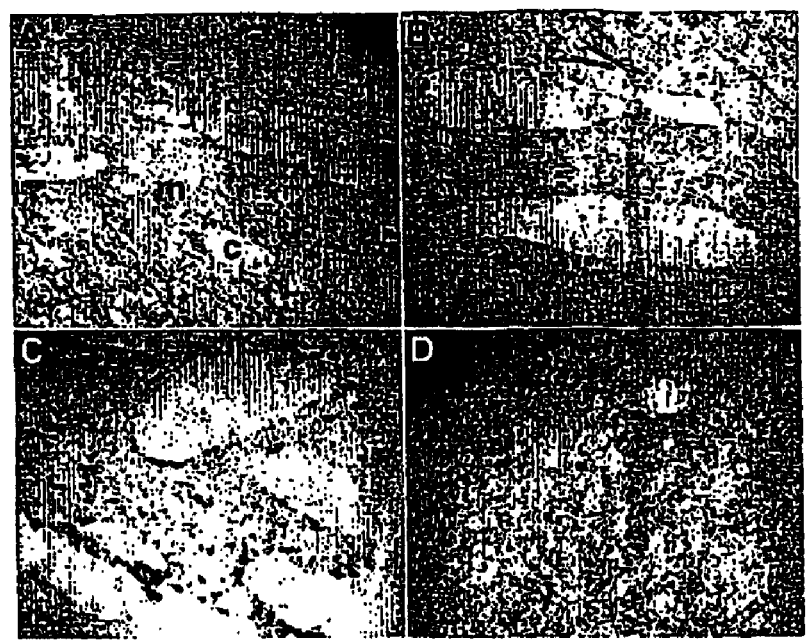

In the experiment as depicted in FIG. 5, by using the in-situ-hybridization studies it was shown that no silicatein-positive cells are present in tissues of sponges that were held in silicate/Fe(+++)-free sea-water. Interestingly, the silicatein-positive cells first appear in the layer of the epithelium (pinacoderm), and only later, four days after the silicate/Fe(+++)-exposition, also cells in the mesohyl were positive with the silicatein-probe (B–D).

3. PRODUCTION OF THE SILICATEIN-β-POLYPEPTIDES

The silicatein-β-polypeptide can be purified from tissues or cells or produced recombinantly.

3.1. Purification of the Silicatein-β-polypeptide from Natural Sources

The purification of the silicatein-β advantageously can be achieved from isolated spiculae of sponges. With the use of this procedure, the silicatein-β-polypeptide can be purified, amongst others, from the sponge S. domuncula.

For this, the spiculae (consisting of amorphous silicate) are obtained from the sponge, e.g. Suberites domuncula, by dissociation of the tissues in $Ca^{++}$- and $Mg^{++}$-free sea-water, and sedimentation. The amorphous silicate of the spiculae is removed in the alkaline milieu, e.g. in diluted sodium hydroxide. The organic fibrils of the spiculae that contain silicatein-β are obtained by centrifugation (e.g. 20,000×g; 1 hour; 4° C.). The protein is brought into solution by a high salt concentration, such as, e.g., 1 M NaCl, but also by the "protein refolding-kit".

Subsequently, the silicatein-β is purified on an affinity matrix. The affinity matrix is produced in that a silicatein-β-specific antibody is immobilized on a solid phase (CNBr-activated sepharose or other suitable carriers). As antibody, monoclonal or polyclonal antibodies against the silicatein-β are used that are produced according to standard methods (Osterman, L. A. Methods of protein and Nucleic Acid Research Vol. 2; Springer-Verlag [Berlin] 1984). The coupling of the antibody to the column matrix is performed according to the instructions of the manufacturer (Co. Pharmacia). The elution of the pure silicatein-β occurs by means of change of pH, or change of the ionic strength.

3.2. Production of Recombinant Silicatein-β-polypeptide 3.2.1. Cloning of the cDNA from Marine Sponges The cloning of the silicatein-β-cDNA from the marine sponge S. domuncula was described above.

The silicatein-β-gene can also be identified with suitable degenerated primers from cDNA-libraries, e.g., in ZapExpress and in Escherichia coli XL1-Blue MRF', by means of the PCR-technique; for this, respective vector specific primers are used. The obtained synthesis products are used for screening the respective cDNA-libraries. Then, the clones as identified are subcloned into a vector (for example pGem-T), and subsequently sequenced.

3.2.2. Expression and Isolation of the Recombinant Silicatein-β-polypeptide

The production of recombinant silicatein-β-polypeptide preferably takes place in E. coli. Nevertheless, the production in yeast and mammalian cells is possible and were successfully performed. For this the cDNA is cloned into a corresponding vector, e.g. pQE-30. Following transformation of E. coli the expression of the silicatein-β-polypeptide is performed by induction with IPTG (isopropyl-β-D-thiogalactopyranoside) (Ausubel et al. (1995) Current Protocols in Molecular Biology. John Wiley and Sons, New York). The expression of the silicatein-β-polypeptide as well as the purification of the recombinant proteins via, e.g., the histidine-tag that is present at the recombinant protein can be performed on corresponding affinity columns, e.g. a Ni-NTA-matrix (Skorokhod et al. (1997) Cell. Mol. Biol. 43:509-519). In the following the expression of the silicatein-β-gene of *S. domuncula* in *E. coli* using the "GST (glutathione-S-transferase) fusion"-system (Co. Amersham) is described as an example. In the example, an insert is used that comprises merely the amino acids $aa_{48}$ to $aa_{383}$ (short form); also an insert can be used that comprises the complete protein as derived. The corresponding clone is cloned into a vector, e.g. into the plasmid pGEX-4T-2, that contains the GST-gene of *Schistosoma japonicum*. Also other expression vectors have been found suitable. Following transformation of *E. coli*, the expression of the silicatein-β-polypeptide is commonly induced by IPTG and performed for 4 or 6 hours at 37° C. (Ausubel F M, Brent R, Kingston R E, Moore D D, Smith J A, Seidmann J G, Struhl K (1995) *Current Protocols in Molecular Biology*. John Wiley and Sons, New York). The GST-fusion protein as obtained is, e.g., purified by affinity chromatography on glutathione-sepharose 4B. For a separation of the glutathione-S-transferase from the recombinant sponge-silicatein-β-polypeptide, the fusion protein is cleaved with thrombin (10 units/mg). The protein is then subjected the gel electrophoresis in the presence of 2-mercaptoethanol. The gel electrophoresis can be performed in 10% polyacrylamide gels with 0.1% $NaDodSO_4$ (polyacrylamide gel-electrophoresis; PAGE). The gel is stained with Coomassie brilliant blue. Following the cleavage, purification and subsequent PAGE, the short form of the recombinant protein is obtained.

3.2.3. Expression and Isolation of the Recombinant Silicatein-β-polypeptide from other Organisms Corresponding to the above described procedure, the isolation, cloning and expression of the silicatein-β-cDNA also from other organisms can be performed, for example from (silicon dioxide-producing) hexactinellida (e.g. *Rhabdocalyptus dawsoni*).

3.3. Isolation and Purification of the Silicatein-β-polypeptide by Means of Antibodies Subsequent to extraction or partial purification according to one of the above described methods, the silicatein-β is purified on an antibody-affinity matrix. The procedure corresponds to those that were described in section 3.1 ("purification of the silicatein-β-polypeptide from natural sources").

Also other affinity matrices, such as polymeric silicates or copolymers silicate/germinate, have been successfully used.

4. DETECTION OF THE SILICATEIN-β-ACTIVITY AND SYNTHESIS OF SILICON-ALKOXY-COMPOUNDS

In the following, only the activities are given that were found for the short form of the recombinant sponge-silicatein-β-polypeptide.

4.1. Silicatein-β-activity 4.1.1. Polymer (e.g. Silica)-forming Activity

For detection of the enzymatic activity of the recombinant silicatein-β, an assay can be used that is based on measuring of polymerized and precipitated silicate after hydrolysis and subsequent polymerization of tetraethoxysilane (TEOS).

The measuring of the enzymatic synthesis-activity of the recombinant silicatein-β is normally done as follows. The recombinant silicatein-β is dialyzed over night against a buffer that is suitable for the reaction, such as 50 mM MOPS, pH 6.8 [other buffers within a pH-range of 4.5 to 10.5 are also suitable].

1-50 µg recombinant silicatein-β were dissolved in 1 ml of a suitable buffer, such as 50 mM MOPS (pH 6.8), and 1 ml of a 1-4.5 mM tetraethoxysilane solution was added. The enzymatic reaction can be performed at room temperature. At an incubation time of 60 min, usually 200 nmol of amorphous silicate (as molybdate-reactive, soluble silicate) per 100 µg silicatein-β are synthesized. For the detection of the silicate products the material is centrifuged in a benchtop centrifuge (12 000×g; 15 min; +4° C.), washed with ethanol, and air-dried. Subsequently, the sediment is hydrolyzed with 1 M NaOH. In the resulting solution silicate is quantitavely measured using a molybdate-supported detection method, such as e.g. the silicone-assay (Merck).

Surprisingly, it was found that silicatein-β, in addition to the substrate tetraethoxysilane, also polymerizes additional silane-alkoxides.

The following compounds can be used as reactants (substrates) for the carboxypeptidase-mediated synthesis: tetraalkoxysilane, trialkoxysilanoles, dialkoxysilandioles, monoalkoxysilantrioles, dialkoxysilanoles, monoalkoxysilandioles, monoalkoxysilanoles, alkyl-, aryl- or metallo-trialkoxysilanes, alkyl-, aryl- or metallo-silanoles, alkyl-, aryl- or metallo-silandioles, alkyl-, aryl- or metallo-silantrioles, alkyl-, aryl- or metallo-monoalkoxysilandioles, alkyl-, aryl- or metallo-dialkoxysilanoles, or other metal(IV)-compounds (alkoxy-compounds of gallium (IV), tin (IV) or lead (IV). Also mixtures of these substrates are recognized by the enzyme, and polymerized. Thus, also mix-polymers can be produced.

The substrates, such as tetraethoxysilane, were dissolved in dimethylsulfoxide in a stock solution of commonly 500 mM, and subsequently diluted down to the desired final concentration.

The silicatein reaction can also be combined with other reactions known from the silicon-chemistry, such as the Müller-Rochow-synthesis of chloro-methylsilanes, the synthesis of longer-chain silanes (e.g. $Si_8$-silanes), and silicon-nitrogen-compounds (e.g. silicon nitrite, $Si_3N_4$). The latter compound is generated through the combustion of silanes through nitrogen or air (air-nitrogen). Longer-chain silanes are generated pyrolytically, e.g. in the presence of copper at 500° C. The large scale technical synthesis of methylsilicones mainly takes place via the Müller-Rochow-method (catalyst: copper; temperatures of between 250-300° C.). These methods are state of the art. Lower silanes are very unstable and are highly-inflammable—under heavy explosions—in the air or upon contact with water, whereas higher (longer-chain) silanes that are no longer self-inflammatory (starting from n-heptasilane) represent promising energy sources (combustibles or fuels). The combustion-product of these silanes is—non-poisonous—silicon nitrite ($Si_3N_4$). Since the enzymatic reaction as catalyzed by silicatein delivers precursors to these silanes, this results in a clear facilitation and improvement of the efficiency and specificity of their synthesis.

As an example that does not limit the scope of the patent claims, the following reaction scheme is given: Thereby short-chain silicates with a chain length of $Si_n$ with n>8 are produced by the biocatalyst silicatein. The hydroxyl groups in these short-chain silicates are replaced in an electrically induced hydrolysis with hydrogen, a reduction agent that releases hydrogen, or by hydrogenations that are catalyzed by Lewis-acids. The water as released is removed from the reaction mixture by suitable methods, corresponding to the state of the art for reduction- and drying methods, or by distillation methods. The reaction scheme can formally be given as follows:

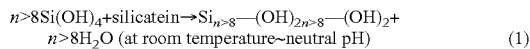

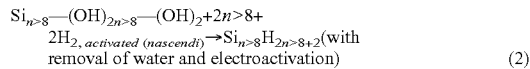

According to the invention a two-step-process can be designed. Electrochemically, hydrogen can be produced from water. For this, a multitude of methods are known. In parallel to this, in one apparatus but spaced apart, according to the invention by the catalytic polypeptide silicatein α and β, oligosilicates with $Si_n(OH)_{2n+2}$ with $n \geq 7$ are formed at—in contrast to the state of the art—extremely mild conditions. Following removal of the reaction solution in a subsequent reaction with activated hydrogen$_{nascendi}$ the oligosilicates can be converted to oligosilanes, corresponding to the formula $Si_n(H)_{2n+2}$ with $n \geq 7$ by hydrogenation. This reaction layout is possible, since-silanes starting from n=7, and corresponding to the formula $Si_n(OH)_{2n+2}$, no longer spontaneously react with oxygen from the air or water, since their activation energy potential increases together with an increasing number n. In contrast, with the lower silanes, a spontaneous reaction takes place, due to the low activation energy potential.

The present invention thus also contributes to the introduction of energy saving and environment-friendly methods, since, amongst others, the chlorinated silicate-compounds as currently used become dispensable. Furthermore, the overall reaction scheme can be performed under extremely mild reaction conditions. With the present invention, oligosilicates can be used as hydrogen source, which can be transported and stored universally, with lower risks and with low technical effort.

According to the invention, with silicatein α and β as catalytic polypeptides as described before, short-chain oligosilicates with n>2 can be produced. In contrast to the state of the art, where temperatures of >200° C. and pressures of above normal pressure are used, here, temperatures of below 50° C. and normal pressure are sufficient. Furthermore, the reaction can be performed in aqueous medium, which is not possible according to the state of the art. This constitutes an essential improvement of the environmental impact, the safety, and also a reduction of costs. In the following reaction schemes, the oligosilicates form the basis for a multitude of products that are currently used, such as silanes, silicones, and other organic silicon compounds.

Due to its reversibility, the silicatein-reaction also allows for a mix-ether-production (formation of Si—O—C bonds), as explained above. Starting from these compounds—according to the state of the art—halogen compounds (e.g. with chlorine) can be formed using other catalysts, from which different silane-compounds can be obtained under a hydrogen-atmosphere.

Silicatein, in particular, is able to synthesize and degrade germanium and titanium compounds, and is also suitable for the production of Si—Ti, Si—Ge or Si—Ge—Ti mix-structures that are of importance for the chip-production.

4.1.2. Polymer (e.g. Silica)-degrading Activity(Silica-dissolving Activity)

Silicatein-β can also dissolve silica, in particular if the reaction takes place in the presence of ascorbic acid or another, catechol or 1,2-diphenol-enthaltenden compound. As a substrate for silicatein-β, for example, spiculae (amorphous silicon dioxide) of S. domuncula can be used.

The spiculae can be obtained from sponge tissue by 12-hour incubation in the presence of ethylenediaminetetraacetic acid (20 mM, in PBS; PBS=phosphate buffer-salt-solution, consisting of 1.15 mM $KH_2PO_4$, 8.1 mM $Na_2HPO_4$, 137 mM NaCl, and 2.7 mM KCl). After washing with distilled water and with ethanol (twice), the spiculae are dried (56° C.), and then grinded to a powder in a mortar.

The silica dissolving activity can then be detected as follows. Commonly, 100 μg of the dried spiculae (powder) are added to a suitable buffer, such as 50 mM tris-HCl-buffer (pH 7.2; 10 mM DL-dithiothreitol, 100 mM NaCl), and 0.5 mM. $ZnSO_4$ in 2 ml Eppendorf-tubes. Then, normally 50 μl of the recombinant silicatein-β-polypeptide are added, and incubated at 25° C. (the incubation is also possible at other temperatures of between 5° C. and about 65° C.). The average incubation time is 60 minutes. For the quantitative detection of the of dissolved silicon dioxide, the non-dissolved spiculae are centrifuged (14000×g; 1.5 minutes; 4° C.). The soluble silicic acid as released can be quantitatively detected, e.g., by using a molybdate-supported detection method, such as, e.g., the colorimetric "silicon test" (Merck; 1.14794). In this case, the amount of silicic acid is calculated from the extinction values at 810 nm, based on a calibration curve with a silicon standard (Merck 1.09947).

4.1.3. Silicon (IV)-compound-synthesizing Activity

The reversibility of the alkoxysilane hydrolyzing activity of the silicatein-β (but also of further silicateins, such as silicatein-α) can also be used for the synthesis of other silicon (IV)-compounds or other metal(IV)-compounds, namely in that the group to be introduced, preferably nucleophilic group, the alkoxysilane (alkoxy-metal(IV)-compound) and the enzyme containing reaction mix are added. In addition to tetraalkoxysilanes, such as, e.g., tetraethoxysilane (TEOS), also trialkoxysilanes, dialkoxysilanes, and monoalkoxysilanes as well as trialkoxysilanoles, dialkoxysilandioles, dialkoxysilanoles, monoalkoxysilantrioles, monoalkoxysilandioles, monoalkoxysilanoles as well as alkyl-, aryl- or halogen-substituted alkoxy compounds of the silicon(IV) can be used.

The silicon(IV)-compound synthesizing activity of the silicatein-β can also be coupled with the polymerization of these substrates or mixtures of these substrates or the products that are generated from them, wherein it is possible to perform the reactions simultaneously in the same preparation. Thus, different polymers or mix-polymers can also be produced.

4.1.4. Coupled Optical Test for Determining the Silicatein-reaction

A simple test for determining the enzymatic activity of the silicatein is given. This constitutes a coupled optical test for determining the alcohol that is released from substrates (alkoxysilanes and derivatives) by the enzymatic reaction that is mediated by silicatein. For this, a photometer is required (e.g. Eppendorf photometer 1101 M). The following buffer solutions are used:

Solution 1

2 mmol/l ABTS (azino-bis(3-ethylbenzthiazoline-6-sulfonic acid)) in buffer, produced as follows:

Step a: 0.1 M sodium phosphate buffer (pH 7,5), prepared from solution A (8.16 g $KH_2PO_4$ dissolve in aqua bidest, add to 600 ml) and solution B (68.4 g $K_2HPO_4$ dissolve in aqua bidest, add to 300 ml; =10× preparation), namely 300 ml solution A with solution B are brought to pH 7.5.

Step b: 320 ml of the solution as produced in step a are saturated with $O_2$ for 30 min; then 352 mg ABTS are dissolved therein. (note: ABTS is light- and air-sensitive, do not use buffer for more than 1 h).

Solution 2

POD (peroxidase, Co. Roche); 10 mg protein/ml, specific activity ca. 5 U/mg.

Solution 3

Alcoholic oxidase (Co. Sigma)-solution, prepared as follows:

Step a: 100 mg BSA are dissolved in 0.1 M sodium phosphate buffer (pH 7.5).

Step b: 10 mg alcoholic oxidase-lyophilisate are dissolved in 1 ml of the BSA-0.1 M sodium phosphate-buffer (cold) as prepared in step a.

Step c: 135 A1 of the alcoholic oxidase-solution as prepared in step b are diluted with 10 ml BSA-0.1 M sodium phosphate buffer (cold) as prepared in step a.

$H_2O_2$

5 μl (Co. Merck) are diluted with aqua bidest to 50 ml.

As substrate solution, for example, 4.5 mM tetraethoxysilane (TEOS) in MOPS-buffer (100 mM NaCl, 5 mM $CaCl_2$, 0.1 mM $ZnSO_4$, pH 6.8) can be used.

The assay is done as follows:

Pipet into cuvette:

2.8 ml buffer/ABTS

10 μl POD

50 μl AO

Then mix, and then addition of

10 μl $H_2O_2$

Mix again, nullification of the photometers (adjust to 0.1), then

Addition of 100 μl substrate solution or enzyme (silicatein) in substrate solution, mix, follow extinction over at least 2 min (filter 405 nm).

Different alcohol (e.g. ethanol)-concentrations serve as positive control and for the calibration curve.

5. LIGATION OF THE CDNA FOR SILICATEIN-β WITH ONE OR SEVERAL CDNA(S) FOR OTHER PROTEINS 5.1. Production of Silicatein-β-fusion Proteins For the production of fusion proteins with the silicatein-β-polypeptide, a suitable expression vector (for example pQE-30-vector; Qiagen) is used. The silicatein-β-cDNA—with, e.g., a BamHI-restriction site at the 5'-terminus and e.g. a SalI-restriction site at the 3'-terminus—is produced. The stop codon in the silicatein-β-cDNA is removed. For this, the PCR-technique is used, and for the amplification primers are used that have the respective restriction sites. The cDNA for the second protein is obtained respectively, wherein on the 5'-terminus the identical restriction site as on the 3'-terminus of the silicatein-β-cDNA (in the example SaiI) and on the 3'-terminus one that is different from the others (e.g. a HindIII-site) is present. If internal restriction sites are present in the respective cDNAs, alternative restriction enzymes can be used. In addition, also linkers can be introduced between both cDNAs.

Both cDNAs are ligated according to the common method, purified and ligated into the pQE-30-vector. The ligation takes place following the histidine-tagging (about 6 histidine-codons). The expression and purification of the fusion protein via e.g. the histidine-tag which is present in the recombinant protein, can be performed on a corresponding affinity column, e.g. a Ni-NTA-matrix (Skorokhod A, Schäcke H, Diehl-Seifert B, Steffen R, Hofmeister A, Müller W E G (1997) Cell Mol Biol 43:509-519).

5.2. Separate Expression I (Protease-cleavage Site)

Alternatively to the method at 5.1., a protease-cleavage site (such as, e.g., an enterokinase-site) can be cloned between the cDNA for the silicatein-β-polypeptide and the cDNA for an additional protein. In this case a codon for a new start-methionine can be inserted before the coding region of the gene for the additional protein. Following expression and purification, the fusion protein is cleaved proteolytically. Now, both proteins are present separately.

5.3. Separate Expression II (Cassette-Expression)

Alternatively both proteins can be separately expressed on one construct. For this, in an expression-vector the silicatein-β-gene is positioned behind the his-tag. At the end of the silicatein-β-cDNA, a stop-codon is inserted. Between the cDNA for the silicatein-β-polypeptide and the cDNA for the additional protein a ribosome-binding site with a codon for a start-methionine is cloned. Again, a his-tag is positioned in front of the cDNA for the additional protein. Also this gene gets a stop-codon.

The his-tags can be deleted, when the proteins are used for functional analysis in the respective host cells.

5.4. Extensions

For the expression as described at 5.1 to 5.3 bacterial as well as eukaryotic cells can be used. The expression as described at 5.1 to 5.3 can also be used for three and more open reading frames.

6. Uses of the Silicatein-β-polypeptide and the Silicatein-β-fusion Proteins

A further aspect of the invention are the uses of the recombinant silicatein-β-polypeptide, the silicatein-β purified from different sources, and the silicatein-β-fusion proteins as indicated in the following. The methods that form the bases of these uses can be readily derived by the person of skill from the disclosure as already given here and above, the respective literature, and by means of the general skill.

1.) Use for the surface modification of biomaterials (improvement of the biocompatibility). Surface-modified biomaterials are used, amongst others, e.g. in a use for influencing of cellular adhesion and growth, for modifying the blood-compatibility or the control of the protein-adsorption (e.g. reduction of the adsorption of contact lenses). An overview over the literature can be found in: Ratner B D et al (Eds.) Biomaterials Science—An Introduction to Materials in Medicine. Academic Press, San Diego, 1996. A problem consists in the fact that the conditions that are used for the production of these modifications often have a detrimental (destructive) effect on the biomaterials as used. A "mild" and biomaterial-protective method, compared to the physical/chemical methods as used, is represented by a modification of the surfaces that exclusively relies on biochemical/enzymatic reactions which is made possible with the aid of the method according to the invention (silicatein-β-mediated enzymatic synthesis and—as reversible reaction—enzymatic degradation of $SiO_2$—or siloxane-containing surfaces with the aid of the recombinant/purified silicatein-β-polypeptide). In particular, a use of the recombinant or silicatein-β purified from natural sources follows for the production of surface-modifications (during coating) of silicone-materials, such as silicone-breast-implants, endoprostheses or metal-implants (improvement of the connection between bone and metal-implant, biologization of the metal-implants) as well as contact/plastic lenses. Further uses relate to the coating of collagen that is used as bone replacement material, and of collagen-fleeces that are, e.g. used for the "tissue engineering". Here, the aim is the increase of the stability and the porosity as well as the improvement of the resorbability.

2.) Use for producing novel biomaterials, such as bone replacement materials or dental replacement materials by co-synthesis of polysilicates, silicones or mix-polymers.

3.) Use for the surface-modification (contact zone-treatment) of (silicon)-semiconductors or silicon-chips.

4.) Use for the modification or the synthesis of nanostructures of amorphous silicon dioxide. By means of the recombinant silicatein-β, the recombinant silicatein-β-fusion proteins or the purified silicatein-β it is possible, to modify or to synthesize specific two- and three-dimensional structures from amorphous silicon dioxide in the nanoscale. The formed structures can be used in the nanotechnology.

5.) Use for the surface-modification of silicon-containing precious stones and semi-precious stones. Agate, jasper, and onyx, amongst others, belong to the amorphous or fine crystalline modifications of the $SiO_2$. Due to the possibility to modify the surface of these minerals with the aid of the silicatein-β under controlled conditions, follows the use of the method according to the invention in the production or processing of these precious stones/semi-precious stones. Here, also the possibility follows, to selectively introduce foreign molecules/atoms.

6.) Use for producing coatings for metals, metal oxides, plastics and other materials; in particular for the production of mono-molecular layers on these materials.

7.) Use for producing coatings for technical fiber materials, e.g. carbon fibers, for fire protection, for the purposes of a better processing or further modification of the properties of these materials.

Carbon fibers (carbon fibers) are of great technical importance, since, compared to metals, essentially lighter, but nevertheless more solid and stiffer components can be produced by using them (particularly important in aviation and astronautics).

8.) Use for producing coatings for wool or cotton for obtaining new properties, in particular anti-allergic properties, an improvement of the purification or further modifications of the properties of these materials. Particularly this case makes clear the advantage of an enzymatic methods, since these materials are sensitive against the drastic conditions that are required during the present methods. With the aid of the silica-coatings, it can be avoided that parts of the solutions that are used stick to the materials.

9.) Use for producing coatings/layers for reducing of allergic reactions in case of additives (e.g. starch) for medicaments (tablets).

10.) Use for producing silicon-nitrogen-compounds.

11.) Use for the synthesis of silicon-organic compounds.

12.) Use for producing silica-complexes with polyphosphates that can also be connected by divalent cations.

13.) Use for producing thixotropic materials. Silicatein can also be used for the (enzymatic or partially-enzymatic) production of thixotropic materials. These materials exhibit the characteristic that their viscosity is reduced (or also increased) during shaking or stirring—with a slight chronological delay. Here, the formation and the breaking up of hydrogen bonds between hydrophilic OH-groups at the surfaces of silicate (silicic acid)-nanoparticles plays a role. By suitably choosing the reaction conditions, highly disperse silicic acids (silicates) can be produced with the aid of silicatein. It is state of the art that highly disperse silicic acids represent an efficient thixotropicating agent. Thixotropic liquids and materials are of great technical importance (e.g. for colors for painting).

14.) Facilitation of the membrane transmissibility of medicaments or RNAs and DNAs by silicatein-mediated coating or encapsulation into silica.

The invention claimed is:

1. An isolated silicatein-β polypeptide from *Suberites domuncula* comprising SEQ ID NO: 1 or a metal complex thereof of the polypeptide.

2. The polypeptide according to claim 1, characterized in that the polypeptide is produced synthetically.

3. The polypeptide according to claim 1, characterized in that the polypeptide or the metal complex thereof of the polypeptide is present in a prokaryotic or eukaryotic cell extract or lysate.

4. The polypeptide according to claim 3, characterized in that the polypeptide or the metal complex thereof of the polypeptide is present essentially free from other proteins.

* * * * *

UNITED STATES PATENT AND TRADEMARK OFFICE
CERTIFICATE OF CORRECTION

PATENT NO. : 7,794,992 B2
APPLICATION NO. : 10/578959
DATED : September 14, 2010
INVENTOR(S) : Werner E. G. Müller, Heiko Schwertner and Heinz-Christoph Schröder Page 1 of 1

It is certified that error appears in the above-identified patent and that said Letters Patent is hereby corrected as shown below:

Title Page
(30) Foreign Application Priority Data, "103 52 433" should read --103 52 433.9--

Column 1
Line 9, "The present invention relates to the use of recombinant" should read
--Description The present invention relates to the use of recombinant--

Column 6
Lines 32 and 33, "(SLLICAaTETHYA" should read --(SILICAaTETHYA--

Column 7
Line 54, "silicatein-β" should read --silicatein-α--

Column 9
Line 10, "Fe (II)" should read --Fe(+++)--

Column 14
Line 18, "1.5 minutes" should read --15 minutes--

Column 15
Line 15, "135 Al" should read --135 µl--
Line 56, "SaiI)" should read --*SalI)*--

Signed and Sealed this
Fifth Day of April, 2011

David J. Kappos
*Director of the United States Patent and Trademark Office*

UNITED STATES PATENT AND TRADEMARK OFFICE
Certificate

Patent No. 7,794,992 B2                                          Patented: September 14, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Werner E. G. Müller, Wiesbaden (DE); Heiko Schwertner, Schwerin (DE); Heinz C. Schröder, Wiesbaden (DE); and Xiaochong Wang, Mainz (DE).

Signed and Sealed this Thirtieth Day of September 2014.

*MANJUNATH RAO*
*Supervisory Patent Examiner*
Art Unit 1656
Technology Center 1600

SEQUENCE LISTING

```
<160> NUMBER OF SEQ ID NOS: 5

<210> SEQ ID NO 1
<211> LENGTH: 383
<212> TYPE: PRT
<213> ORGANISM: Suberites domuncula

<400> SEQUENCE: 1

Met Ser Ala Leu Lys Phe Val Val Ala Leu Cys Val Val His Thr Ser
1               5                   10                  15

Leu Gly Ile Ala Glu Ser Val Gly Lys Ser Lys Thr Ala Gly Leu Ser
            20                  25                  30

Asp Asp Gly Asn Tyr Thr Ala Val Thr Lys Ser Val Arg Leu Thr Pro
        35                  40                  45

Val Leu Glu Phe Glu Glu Asp Trp Lys Gln Trp Thr Thr Asp His His
    50                  55                  60

Lys Val Tyr Ser Asp Val Arg Glu Arg Val Asp Lys Tyr Thr Val Trp
65                  70                  75                  80

Arg Ala Asn Lys Glu Tyr Ile Asp Gln His Asn Gln Asn Ala Gln Arg
                85                  90                  95

Leu Gly Tyr Thr Leu Lys Met Asn Lys Phe Gly Asp Leu Thr Thr Lys
            100                 105                 110
```

Glu Phe Ile Glu Gly Tyr His Cys Val Gln Asp Tyr Gln Pro Thr Asn
    115                 120                 125

Ala Ser His Leu Asn Lys Lys His Lys Thr His Ala Phe Val Asp Tyr
130                 135                 140

Gly Asp Phe Val Arg Gly Gly Thr Gly Glu Gly Val Arg Gly Val Gly
145                 150                 155                 160

Asn Met Pro Glu Thr Met Asp Trp Arg Thr Ser Gly Val Val Thr Lys
                165                 170                 175

Val Lys Asp Gln Leu Arg Cys Gly Ser Ser Tyr Ala Phe Ser Ala Met
            180                 185                 190

Ala Ser Leu Glu Gly Ile Asn Ala Leu Ser Tyr Gly Ser Leu Val Thr
        195                 200                 205

Leu Ser Glu Gln Asn Ile Val Asp Cys Ser Val Thr Tyr Gly Asn His
    210                 215                 220

Gly Cys Ala Cys Gly Asp Val Asn Arg Ala Leu Leu Tyr Val Ile Glu
225                 230                 235                 240

Asn Asp Gly Val Asp Thr Trp Lys Gly Tyr Pro Ser Gly Gly Asp Pro
                245                 250                 255

Tyr Arg Ser Lys Gln Tyr Ser Cys Lys Tyr Glu Arg Gln Tyr Arg Gly
            260                 265                 270

Ala Ser Ala Arg Gly Ile Val Ser Leu Ala Ser Gly Asp Glu Asn Thr
        275                 280                 285

Leu Leu Thr Ala Val Ala Asn Ser Gly Pro Val Ser Val Tyr Val Asp
    290                 295                 300

Ala Thr Ser Thr Ser Phe Gln Phe Tyr Ser Asp Gly Val Leu Asn Val
305                 310                 315                 320

Pro Tyr Cys Ser Ser Ser Thr Leu Ser His Ala Leu Val Val Ile Gly
                325                 330                 335

Tyr Gly Lys Tyr Ser Gly Gln Asp Tyr Trp Leu Val Lys Asn Ser Trp
            340                 345                 350

Gly Pro Asn Trp Gly Val Arg Gly Tyr Gly Lys Leu Ala Arg Asn Lys
        355                 360                 365

Gly Asn Lys Cys Gly Ile Ala Thr Ala Ala Ser Phe Pro Thr Leu
    370                 375                 380

<210> SEQ ID NO 2
<211> LENGTH: 1372
<212> TYPE: DNA
<213> ORGANISM: Suberites domuncula

<400> SEQUENCE: 2
acttagtata ttatggtagt gtacaatacc tatctccata gaggcatgca taactaggtt      60
tattgaatag ctgctggcac aatttgttct caagttggtg ctattagatt tgtgttctag     120
aatgtcagca ttgaagtttg tagttgcctt gtgtgtagtt cacacaagct taggaatagc     180
tgagtcagtt ggtaagagca agactgcagg cctaagtgac gatggcaact acacagctgt     240
caccaaatct gtaagactga ctccagttct agagtttgag gaagattgga agcaatggac     300
aactgatcat cacaaggtct actctgatgt gagggagaga gtggacaagt acactgtatg     360
gagagctaat aaagagtaca ttgatcaaca caaccagaac gcacagagat gggatacac      420 actcaaaatg aacaaatttg gagatttgac taccaaggag ttcattgaag ctatcactg      480 tgttcaggac taccaaccta ccaatgcatc acatttgaat aagaaacaca aaacgcacgc     540
gtttgtcgac tatggtgact tgtgaggggg tggaactggt gagggtgtga gggtgtagg     600

-continued

```
aaacatgccg agactatgg actggagaac ttctggagtt gtcacaaaag ttaaagatca    660
gcttcgttgt ggtagcagct atgcgttctc tgccatggct tcattggaag aataaatgc    720 tctttcctac ggatctttgg tgacactcag tgaacaaaac attgtagact gctcggttac    780
ctatggcaac catggttgcg cctgtggtga tgtaaaccgt gctctactgt atgtgataga    840
gaatgatggc gttgacacgt ggaagggtta tccttctggt ggggatcctt atcgatcaaa    900
gcaatactct tgcaaatacg agagacagta tcgtggggcc tctgctagag gtatagtcag    960
tctagctagt ggtgatgaga acacattgtt gacagcagta gctaactctg gaccagtgag   1020
tgtgtatgtg gacgctactt caacatcctt ccagttttac agtgatggag tgttgaatgt   1080
tccctattgc tcctctagca cgctgagtca tgccttggtt gtcattggtt acgggaagta   1140
cagcggacaa gattactggc ttgttaaaaa cagctggggt cctaactggg gagtgcgggg   1200
ctatgggaag ttggcaagaa acaagggcaa caaatgtgga atagccacag cggctagttt   1260
cccaacatta tgacacttta gttgatcaaa caattaatca taaattatta caacatgtag   1320
tataatgatg cccccccatt gctcaatagc ttatctttga acaagaaaaa aa           1372
```

<210> SEQ ID NO 3
<211> LENGTH: 330
<212> TYPE: PRT
<213> ORGANISM: Suberites domuncula

<400> SEQUENCE: 3

```
Met Leu Val Thr Val Val Leu Gly Leu Leu Gly Phe Ala Ser Ala
1               5                   10                  15

Ala Gln Pro Lys Phe Glu Phe Val Glu Glu Trp Gln Leu Trp Lys Ser
            20                  25                  30

Thr His Ser Lys Met Tyr Glu Ser Gln Leu Met Glu Leu Glu Arg His
        35                  40                  45

Leu Thr Trp Leu Ser Asn Lys Lys Tyr Ile Glu Gln His Asn Val Asn
    50                  55                  60

Ser His Ile Phe Gly Phe Thr Leu Ala Met Asn Gln Phe Gly Asp Leu
65                  70                  75                  80

Ser Glu Leu Glu Tyr Ala Asn Tyr Leu Gly Gln Tyr Arg Ile Glu Asp
                85                  90                  95

Lys Lys Ser Gly Asn Tyr Ser Lys Thr Phe Gln Arg Asp Pro Leu Gln
            100                 105                 110

Asp Tyr Pro Glu Ala Val Asp Trp Arg Thr Lys Gly Ala Val Thr Ala
        115                 120                 125

Val Lys Asp Gln Gly Asp Cys Gly Ala Ser Tyr Ala Phe Ser Ala Met
    130                 135                 140

Gly Ala Leu Glu Gly Ala Asn Ala Leu Ala Lys Gly Asn Ala Val Ser
145                 150                 155                 160

Leu Ser Glu Gln Asn Ile Ile Asp Cys Ser Ile Pro Tyr Gly Asn His
                165                 170                 175

Gly Cys His Gly Gly Asn Met Tyr Asp Ala Phe Leu Tyr Val Ile Ala
            180                 185                 190

Asn Glu Gly Val Asp Gln Asp Ser Ala Tyr Pro Phe Val Gly Lys Gln
        195                 200                 205

Ser Ser Cys Asn Tyr Asn Ser Lys Tyr Lys Gly Thr Ser Met Ser Gly
    210                 215                 220

Met Val Ser Ile Lys Ser Gly Ser Glu Ser Asp Leu Gln Ala Ala Val
225                 230                 235                 240
```

```
Ser Asn Val Gly Pro Val Ser Val Ala Ile Asp Gly Ala Asn Ser Ala
                245                 250                 255

Phe Arg Phe Tyr Tyr Ser Gly Val Tyr Asp Ser Ser Arg Cys Ser Ser
            260                 265                 270

Ser Ser Leu Asn His Ala Met Val Val Thr Gly Tyr Gly Ser Tyr Asn
        275                 280                 285

Gly Lys Lys Tyr Trp Leu Ala Lys Asn Ser Trp Gly Thr Asn Trp Gly
    290                 295                 300

Asn Ser Gly Tyr Val Met Met Ala Arg Asn Lys Tyr Asn Gln Cys Gly
305                 310                 315                 320

Ile Ala Thr Asp Ala Ser Tyr Pro Thr Leu
                325                 330

<210> SEQ ID NO 4
<211> LENGTH: 330
<212> TYPE: PRT
<213> ORGANISM: Tethya aurantium

<400> SEQUENCE: 4

Met Tyr Leu Gly Thr Leu Val Val Leu Cys Val Leu Gly Ala Ala Ile
1               5                   10                  15

Gly Glu Pro Met Pro Gln Tyr Glu Phe Lys Glu Glu Trp Gln Leu Trp
            20                  25                  30

Lys Lys Gln His Asp Lys Ser Tyr Ser Thr Asn Leu Glu Glu Leu Glu
        35                  40                  45

Lys His Leu Val Trp Leu Ser Asn Lys Lys Tyr Ile Glu Leu His Asn
    50                  55                  60

Ala Asn Ala Asp Thr Phe Gly Phe Thr Leu Ala Met Asn His Leu Gly
65                  70                  75                  80

Asp Met Thr Asp His Glu Tyr Lys Glu Arg Tyr Leu Thr Tyr Thr Asn
                85                  90                  95

Ser Lys Ser Gly Asn Tyr Thr Lys Val Phe Lys Arg Glu Pro Trp Met
            100                 105                 110

Ala Tyr Pro Glu Thr Val Asp Trp Arg Thr Lys Gly Ala Val Thr Gly
        115                 120                 125

Ile Lys Ser Gln Gly Asp Cys Gly Ala Ser Tyr Ala Phe Ser Ala Met
    130                 135                 140

Gly Ala Leu Glu Gly Ile Asn Ala Leu Ala Thr Gly Lys Leu Thr Tyr
145                 150                 155                 160

Leu Ser Glu Gln Asn Ile Ile Asp Cys Ser Val Pro Tyr Gly Asn His
                165                 170                 175

Gly Cys Lys Gly Gly Asn Met Tyr Val Ala Phe Leu Tyr Val Val Ala
            180                 185                 190

Asn Glu Gly Val Asp Asp Gly Gly Ser Tyr Pro Phe Arg Gly Lys Gln
        195                 200                 205

Ser Ser Cys Thr Tyr Gln Glu Gln Tyr Arg Gly Ala Ser Met Ser Gly
    210                 215                 220

Ser Val Gln Ile Asn Ser Gly Ser Glu Ser Asp Leu Glu Ala Ala Val
225                 230                 235                 240

Ala Asn Val Gly Pro Val Ala Val Ala Ile Asp Gly Glu Ser Asn Ala
                245                 250                 255

Phe Arg Phe Tyr Tyr Ser Gly Val Tyr Asp Ser Ser Arg Cys Ser Ser
            260                 265                 270

Ser Ser Leu Asn His Ala Met Val Ile Thr Gly Tyr Gly Ile Ser Asn
```

```
                    275                 280                 285
Asn Gln Glu Tyr Trp Leu Ala Lys Asn Ser Trp Gly Glu Asn Trp Gly
    290                 295                 300

Glu Leu Gly Tyr Val Lys Met Ala Arg Asn Lys Tyr Asn Gln Cys Gly
305                 310                 315                 320

Ile Ala Ser Asp Ala Ser Tyr Pro Thr Leu
                325                 330

<210> SEQ ID NO 5
<211> LENGTH: 334
<212> TYPE: PRT
<213> ORGANISM: Tethya aurantium

<400> SEQUENCE: 5

Met Lys Trp Ile Val Ala Val Cys Met Val Gly Phe Leu Val Ala Val
1               5                   10                  15

Thr Ser Ala Gly Arg His Gln Pro Val Phe Glu His His Glu Glu Trp
                20                  25                  30

Gln Leu Trp Lys Ser Gln His Gly Lys Ser Tyr Arg Ser Gly Leu Gln
            35                  40                  45

Glu Leu Glu Arg His Leu Val Trp Val Ser Asn Lys Glu Tyr Ile Asp
    50                  55                  60

Arg His Asn Ala Asn Ala Asp Val Phe Gly Phe Ser Leu Ala Met Asn
65                  70                  75                  80

His Phe Gly Asp Leu Ser Asp Asn Glu Phe Val Asp Lys Tyr Leu Ser
                85                  90                  95

Tyr Thr Lys Ser Asp Lys Lys Arg Asn Val Lys Met Phe Glu Ala
                100                 105                 110 Ala

Pro Glu Gly Val Ser Tyr Pro Glu Ser Leu Asp Trp Arg Thr Lys Gly
    115                 120                 125

Ala Val Thr Ser Val Lys Asn Gln Gly Asp Cys Gly Ala Ser Tyr Ala
            130                 135                 140

Phe Ser Ala Ile Gly Ser Leu Glu Gly Ala Leu Ser Leu Ala Gln Gly
145                 150                 155                 160

Lys Leu Thr Tyr Leu Ser Glu Gln Asn Val Ile Asp Cys Ser Val Ala
                165                 170                 175

Tyr Gly Asn His Gly Cys Gln Gly Gly Asn Met Tyr Asn Thr Tyr Leu
                180                 185                 190

Tyr Ile Leu Ser Asn Asp Gly Ile Asp Thr Ser Asp Gly Tyr Pro Phe
    195                 200                 205

Lys Gly Lys Gln Thr Ser Cys Thr Tyr Asp Arg Ser Cys Arg Gly Thr
    210                 215                 220

Ser Ile Ser Gly Ser Ile Ala Ile Thr Ser Gly Ser Glu Ser Asp Leu
225                 230                 235                 240

Gln Ala Ala Val Ala Ser Ala Gly Pro Val Ala Val Ala Val Asp Gly
                245                 250                 255

Ser Ser Arg Ala Phe Arg Phe Tyr Asp Tyr Gly Leu Tyr Asn Leu Pro
                260                 265                 270

Gly Cys Ser Ser Tyr Gln Leu Ser His Ala Leu Leu Ile Thr Gly Tyr
            275                 280                 285

Gly Ser Phe Asn Gly Asn Gln Tyr Trp Leu Val Lys Asn Ser Trp Gly
    290                 295                 300

Thr Asn Trp Gly Met Ser Gly Tyr Ile Met Met Thr Arg Asn Asn Tyr
305                 310                 315                 320
```

```
Asn Gln Cys Gly Ile Ala Thr Asp Ala Ala Tyr Pro Thr Leu
                325                 330
```